(12) United States Patent
Uihlein

(10) Patent No.: US 8,562,624 B2
(45) Date of Patent: Oct. 22, 2013

(54) STONE CATCHING BASKET INSTRUMENT AND METHOD FOR PRODUCING THE SAME

(75) Inventor: Bernhard Uihlein, Dettingen (DE)

(73) Assignee: EPflex Feinwerktechnik GmbH, Dettingen/Ems (DE)

( * ) Notice: Subject to any disclaimer, the term of this patent is extended or adjusted under 35 U.S.C. 154(b) by 688 days.

(21) Appl. No.: 12/031,319

(22) Filed: Feb. 14, 2008

(65) Prior Publication Data

US 2008/0208211 A1 Aug. 28, 2008

Related U.S. Application Data

(63) Continuation of application No. PCT/EP2006/007962, filed on Aug. 11, 2006.

(30) Foreign Application Priority Data

Aug. 15, 2005 (DE) .................. 10 2005 040 214

(51) Int. Cl.
*A61B 17/22* (2006.01)

(52) U.S. Cl.
USPC ......................................... 606/127; 606/200

(58) Field of Classification Search
USPC .......... 606/113, 114, 127, 200, 128, 191, 198
See application file for complete search history.

(56) References Cited

U.S. PATENT DOCUMENTS

| | | | |
|---|---|---|---|
| 5,647,870 A | 7/1997 | Kordis et al. | |
| 5,907,893 A | 6/1999 | Zadno-Azizi et al. | |
| 6,013,086 A | 1/2000 | Ouchi et al. | |
| 6,093,196 A * | 7/2000 | Okada | 606/127 |
| 6,168,603 B1 * | 1/2001 | Leslie et al. | 606/114 |
| 6,224,612 B1 | 5/2001 | Bates et al. | |
| 6,327,772 B1 | 12/2001 | Zadno-Azizi et al. | |
| 2003/0120281 A1 * | 6/2003 | Bates et al. | 606/114 |
| 2003/0187495 A1 | 10/2003 | Cully et al. | |
| 2004/0138677 A1 | 7/2004 | Little et al. | |
| 2005/0165442 A1 | 7/2005 | Thinnes, Jr. et al. | |
| 2006/0004404 A1 * | 1/2006 | Khachin et al. | 606/200 |

FOREIGN PATENT DOCUMENTS

| | | |
|---|---|---|
| DE | 101 17 836 C1 | 7/2002 |
| DE | 69716779 T | 7/2003 |
| DE | 10 2004 055 375 A1 | 6/2006 |
| WO | WO 98/36694 A1 | 8/1998 |
| WO | WO 03/017823 A2 | 3/2003 |
| WO | WO 2004/056275 A1 | 7/2004 |
| WO | WO 2004/064597 A2 | 8/2004 |

OTHER PUBLICATIONS

German Office Action dated Apr. 5, 2007 (Three (3) pages).
German Office Action dated Sep. 19, 2007 (Four (4) pages).
International Search Report dated Aug. 11, 2006 with English translation of relevant portion (Twelve (12) pages).
German Office Action dated May 24, 2006 (four (4) pages).

* cited by examiner

*Primary Examiner* — Ryan Severson
*Assistant Examiner* — Katherine M Shi
(74) *Attorney, Agent, or Firm* — Crowell & Moring LLP

(57) ABSTRACT

A stone catching instrument for use, for example, as a stone catching basket and a wire filter unit for medical instruments, and method for producing the same, are provided. The stone catching basket instrument has a multiwire basket unit with several wire sections connected with one another as a cohesive wire complex, the wire complex cut in one piece out of a planar material in a rosette-shape and bent to form the wire basket unit. The wire sections extend essentially radially and are cohesive with one another at their inner radial ends at a wire linkage area. The wire basket unit when in a widened condition is arranged to catch particles caught through spaces between the wire sections, and when moved to a drawn-together condition, holds particles in the wire basket unit.

8 Claims, 4 Drawing Sheets

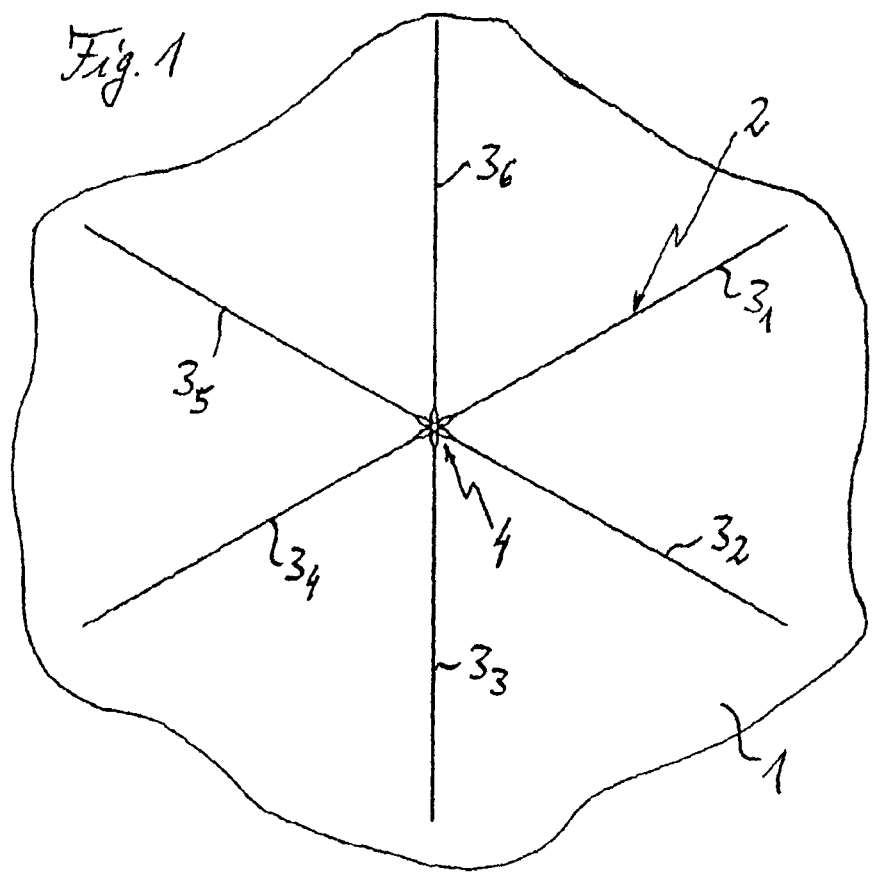
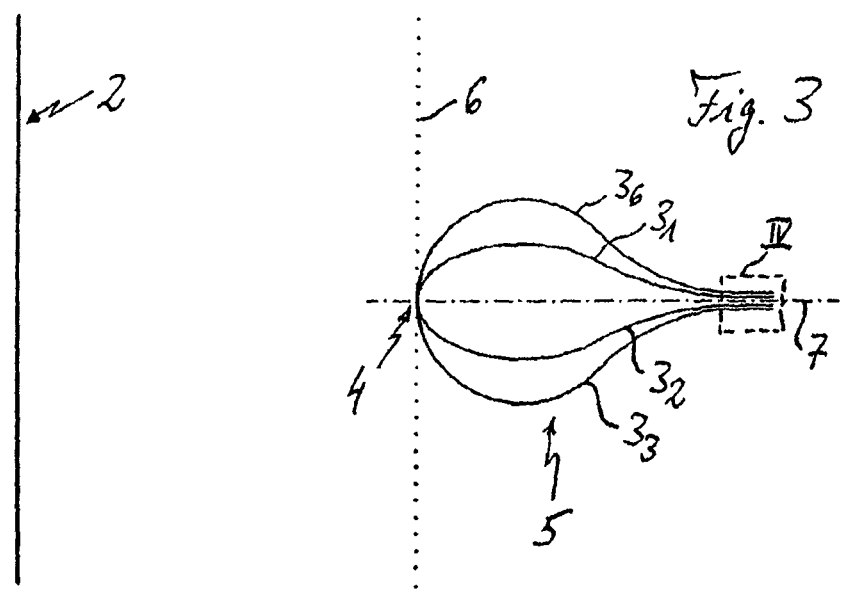

STONE CATCHING BASKET INSTRUMENT AND METHOD FOR PRODUCING THE SAME

CROSS-REFERENCE TO RELATED APPLICATIONS

This application is a continuation of PCT International Application No. PCT/EP2006/007962, filed on Aug. 11, 2006, which claims priority under 35 U.S.C. §119 to European Application No. 10 2005 040 214.3, filed Aug. 15, 2005, the entire disclosures of which are expressly incorporated by reference herein.

BACKGROUND AND SUMMARY OF THE INVENTION

The invention relates to a stone catching basket instrument and to a method of producing such a multiwire basket instrument.

Stone catching basket instruments of this type are used for medical purposes for catching and removing stones or other concretions from human or animal tissue canals. In the present context, the term "wire basket" means that several wire sections are arranged around a longitudinal axis of a thus formed wire basket unit at a distance from one another extending essentially axially in the circumferential direction. In a basket-forming condition, they extend from a forward end area of the wire basket unit, while forming the wire basket, first expanding radially toward the outside and then again narrowing again radially toward the inside. The wire sections consist of a sufficiently elastic, not necessarily metallic material, frequently superelastic metal alloys being used.

Typically, the wire sections, when used as a wire basket, are held in a rearward end area by a receiving sleeve into which they can be pulled while the wire basket shrinks radially. In the pulled-out basket-forming condition, a stone or the like can move into the widened wire basket through the spaces between the wire sections, after which, by the pulling of the wire sections into the receiving sleeve, the wire basket is drawn together and the stone can be retained for the removal.

Medical stone catching basket instruments of this type are used in various designs, for example, for endoscopes. In the case of these applications, a forward end of the wire basket which is as short as possible is frequently desirable. In constructions, as disclosed, for example, in U.S. Pat. No. 6,013,086, the forward wire section ends or forward end bows of wire loops are held in a cylindrical end sleeve which therefore remains disposed in front of the actual wire basket area. In contrast, so-called tipless wire basket units have been suggested. Thus, International Published Patent Application WO 98/36694 A1 describes wire basket units where the basket-forming wire bows on the forward wire basket end, while forming narrower loops, are mutually linked loosely and thereby in an articulated manner. In German Patent Document DE 101 17 836 C1, it is suggested that the wire sections at the forward end be held in an articulated manner on a fixing body which may be designed such that, in the basket-forming condition, a virtually tipless forward end of the wire basket unit is obtained.

In the applicant's German Published Patent Application DE 10-2004-055375 A1, which is a later publication, a multiwire basket unit and a method of producing the same are described, which are based on a tubular piece from which the multiwire basket unit is formed in one piece, for the purpose of which the tubular jacket is subdivided into the wire sections by several axial slots spaced in the circumferential direction. The axial slots end while leaving a wire linkage area at a distance in front of a tube front end, and the wire sections are subsequently bent at the wire linkage area into a predefinable functional state. The content of this earlier patent application is thereby fully included here by reference in order to avoid unnecessary repetitions of text.

In the following, reference is made to this earlier patent application in an abbreviated manner as the "older application."

A stone catching basket instrument of the initially mentioned type is disclosed in International Published Patent Application WO 2004/064597. In the case of this stone catching basket instrument, the wire linkage area is constructed as a centric predetermined breaking point area from which the individual wire sections originate. In this predetermined breaking point area, at least one of the wire sections is weakened or tapered in its thickness or width toward the center, are weakening perforations are provided.

In U.S. Published Patent Application US 2003/0187495 A1, a filtering instrument for endovascular medical applications is disclosed, in which a filter bag is held in a spread-open manner by a filter frame, which is formed by mutually connected wire sections as a cohesive wire complex. In this case, the wire complex is cut in one piece from an essentially plane raw material in a shape, where the wire sections extend essentially radially and are mutually cohesive at their radially interior end area by way of a wire linkage area designed in the shape of a rosette, the wire sections being bent with their free radially exterior ends by approximately 90° in a proximal direction and being guided together. In the distal direction, the filter bag adjoins the wire linkage area of the wire complex. Optionally, the wire complex can also be used as the filter without the filter bag.

U.S. Pat. No. 5,647,870 discloses a wire-basket-type electrode carrier structure for medical catheter applications, which is formed of several wire sections as a cohesive wire complex. In this case, the wire complex is cut in one piece from an essentially plane raw material in a shape in which the wire sections extend essentially radially and are mutually cohesive at their radially interior end area by way of a disk-shaped wire linkage area provided with a central opening. The free radial exterior ends of the wire sections are bent by approximately 90° in a proximal direction and are guided together, at least one of the wire sections consisting of a flexible metallic or plastic material carrying an electrode element.

The invention is based on the technical problem of providing a stone catching basket instrument of the initially mentioned type, which can be implemented at comparatively low expenditures, and a pertaining production method.

The multiwire basket unit of the stone catching basket instrument according to the invention can be formed of a cohesive wire complex, in which the wire sections are connected with one another and which is cut in one piece from an essentially plane raw material, the cut-out wire complex being bent into a wire basket unit. The cut-out wire complex contains essentially radially extending wire sections which are mutually cohesive at a radially interior end while forming a rosette-shaped wire linkage area. For forming the wire basket, the radial wire sections, for example, by means of their radial exterior ends, can be bent out of the cutting plane by approximately 90° and can be guided together. The wire linkage area forms the other axial end of the wire basket unit situated opposite the guided-together wire section ends, specifically the forward wire basket end which is distal when in use. Different designs are conceivable for the rosette-shaped wire basket linkage area, which designs, in turn, determine the shape of the corresponding axial wire basket end area.

The invention thereby permits the production of the multiwire basket unit from a plane raw material, such as a metal sheet or foil material. As required, the wire complex can be designed such that, in the case of a corresponding bending out of the plane, for example, a virtually tipless wire basket is obtained, which is used as a catching basket. The rosette shape of the wire linkage area, which particularly may also be a multiple rosette shape, is particularly advantageous in order to achieve a tipless wire basket end of a high stability and strength and/or permit a secure radial folding-together and re-unfolding of the wire basket, for example, by a pulling or pushing into a receiving sleeve and a pulling out again from a receiving sleeve.

While, during the cutting-out of the wire complex with the cohesive wire sections from a tubular piece, as provided in the older application, attention must possibly be paid to the fact that the cutting operation, for example, by means of a laser beam, does not continue on the respectively opposite tubular jacket side, the cutting of the wire complex out of an essentially plane raw material generally is clearly simpler. Specific characteristics, which may occur as a result of the tubular curvature when cutting the wire complex out of a tubular piece, do not exist from the start when, according to the invention, essentially plane sheet material is used as the raw material. Generally, the use of essentially plane raw material permits a very precise and advantageous guiding and shaping of the cuts during the cutting operation, for example, by means of a cutting laser. Furthermore, plane sheet material is generally more cost effective than tubular material.

In an advantageous embodiment of the invention, the raw material and thus the multiwire basket unit consists of a superelastic material. As a rule, such materials also have a shape memory. The latter can be utilized for selecting the functional state of the wire sections mutually connected in the wire complex as the dimensionally stable state, so that the wire sections will automatically assume their functional state when they are not prevented therefrom by external forces, for example, by the introduction into a receiving sleeve or are changed into a different state.

As a further development of the invention, the cutting-out of the wire complex may take, for example, by laser cutting or water jet cutting.

Other objects, advantages and novel features of the present invention will become apparent from the following detailed description of the invention when considered in conjunction with the accompanying drawings.

BRIEF DESCRIPTION OF THE DRAWINGS

FIG. 1 is a top view of a sheet of raw material with a cut-out wire complex for forming a wire basket unit in accordance with an embodiment of the present invention;

FIG. 2 is a lateral view of the cut-out wire complex of FIG. 1;

FIG. 3 is a lateral view of wire basket unit formed by wire section bending from the cut-out wire complex of FIGS. 1 and 2;

DETAILED DESCRIPTION

Figure 4:
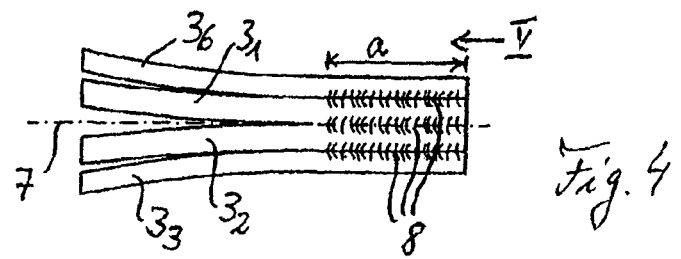
FIG. 4 is a view of a detail of an area IV of FIG. 3.

A sheet material 1 illustrated in the manner of a cutout in FIG. 1 consists of an elastically deformable material, preferably a superelastic material, and is essentially present in a plane shape, for example, as a foil or metal sheet material. A wire complex 2 is cut out of the sheet material 1, for example, by means of laser cutting or water jet cutting. In the illustrated example, the wire complex 2 contains six wire sections $3_1$ to $3_6$ which extend radially toward the outside from an interior wire linkage area 4. The radially interior wire linkage area 4 is constructed in a rosette shape such that the six wire sections $3_1$ to $3_6$ are mutually cohesive there and extend radially toward the outside from there to the free radial exterior ends.

FIG. 2 is a lateral view of the star-shaped wire complex 2 cut out of the sheet material 1. Corresponding to the plane material 1, the cut-out wire complex 2 is plane in this condition.

From this cut-out plane position, the wire sections $3_1$ to $3_6$ are bent over by approximately 90° such that they are guided together with their radially exterior ends, so that a wire basket unit 5 shown in the lateral view in FIG. 3 is formed as a result of the design of the wire linkage area and the elasticity characteristics. In other words, the wire sections $3_1$ to $3_6$ are bent with their radially exterior ends from the cutting plane 6 shown by a dotted line in FIG. 3, that is, the plane of the sheet material 1 of FIG. 1, toward an axis 7 perpendicular thereto and indicated by a dash-dotted line in FIG. 3. The wire sections $3_1$ to $3_6$ remain mutually connected at the rosette-shaped wire linkage area 4 which, in the small-basket-forming condition of the wire complex according to FIG. 3, for example, forms a forward distal end of the wire basket unit 5. In this form, the wire basket unit 5 can be inserted as a stone catching basket unit into medical instruments.

Figure 5:
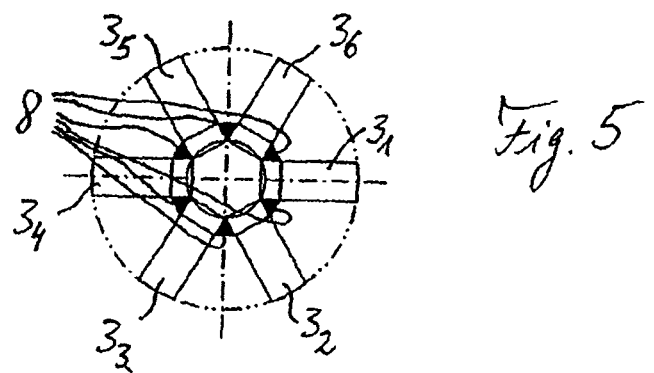
FIG. 5 is a top view of a rearward axial end area of the wire basket unit in the direction of an arrow V of FIG. 4.

FIG. 4 is a more detailed view of the bent-over guided-together ends of the wire sections, in the lateral view of FIG. 4 as well as in the lateral view of FIG. 3, four wire sections $3_1$, $3_2$, $3_3$, $3_6$ of the total of six wire sections $3_1$ to $3_6$ being visible. The wire sections $3_1$ to $3_6$ are fixed to one another at their guided-together axial ends; in the example of FIG. 4, especially by means of welded connections 8. As illustrated in the axial top view of FIG. 5, the wire sections $3_1$ to $3_6$ are guided together with their free axial ends while forming a ring-shaped end, and the fixing welded connections 8 are in each case inserted between two adjoining wire section ends. As shown in FIG. 4, the welded connections 8 are provided along a certain axial length a, so that, along this length a, the wire sections $3_1$ to $3_6$ extend axially in this end area. This measure contributes to a secure end-side mutual fixing of the wire sections $3_1$ to $3_6$ and to a corresponding shaping of the wire basket unit 5 formed by the latter, as illustrated in FIG. 3.

With respect to further advantages and characteristics of wire basket units shaped in this manner for the use in medical stone catching basket instruments, reference can be made to corresponding statements in the older application. In particular, the characteristic of a virtually tipless distal end closure of the wire basket unit 5 as a result of the characteristics of the linkage area 4 should be stressed. Particularly the rosette-shaped design of the wire linkage area 4 contributes to achieving such a tipless wire basket end closure of high stability and strength and thus of a high reliability of the wire basket unit 5 when it is used. Furthermore, in the present case, the wire basket unit 5 can be produced in a particularly simple manner from the plane sheet material 1. In contrast to a production from a tubular material, the cutting operation can take place in a very simple manner from a raw material that is not curved or is at most slightly curved, and the problem is eliminated that attention must be paid to the respectively opposite tubular jacket side during the cutting into the tubular jacket, which is inherent when a tubular material is used.

FIGS. 6 to 10 show variants of the of FIGS. 1 to 5 with different designs of the wire linkage area. In addition, the same reference symbols as in the of FIGS. 1 to 5 are used for identical or functionally equivalent elements, so that reference can be made to the above description.

Figure 6:
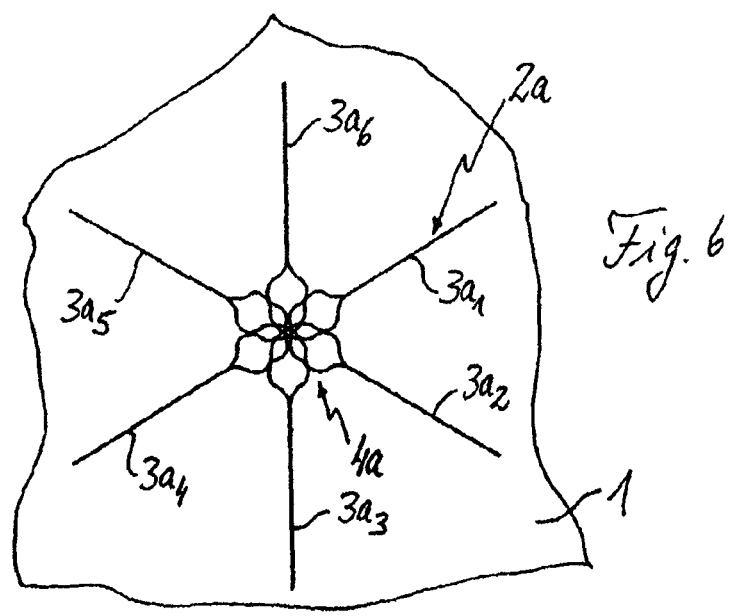
FIG. 6 is a top view of a sheet material with the cut-out wire complex in a variant of FIG. 1.
Figure 7:
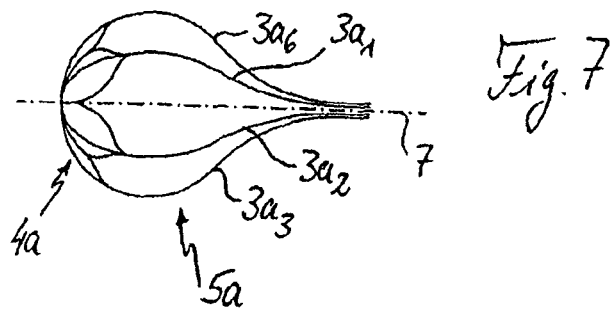
FIG. 7 is a lateral view corresponding to FIG. 3 for a wire basket unit formed of the wire complex according to FIG. 6.

In the variant illustrated in FIG. 6, a wire complex $2a$ consisting of six radially extending wire sections $3a_1$ to $3a_6$ is cut out of the essentially plane sheet material 1, which wire sections $3a_1$ to $3a_6$ have free ends radially on the outside and are cohesive by way of a wire linkage area $4a$ radially on the inside, which wire linkage area $4a$ has a multiple rosette shape. The cut-out wire complex $2a$ can be bent to form a wire basket unit $5a$ illustrated in a lateral view in FIG. 7, in that, as in the example of FIGS. 1 to 5, the free axial ends of the wire sections $3a_1$ to $3a_6$ are bent out of the cutting plane by approximately 90° and are guided together close to a corresponding longitudinal axis $7a$ of the wire basket. Compared with the example of FIGS. 1 to 5, as a result of its more complex multiple rosette shape, as visible in FIG. 6, instead of the single rosette shape of the wire linkage area 4, as visible in FIG. 1, the wire linkage area $4a$ is more flexible for the wire bending operation, so that the wire basket unit extends slightly less steep at its forward distal end defined by the wire linkage area $4a$; that is, the wire sections $3a_1$ to $3a_6$ change from the distal end at a slightly smaller angle with respect to the longitudinal axis 7 of the wire basket 7 into the basket-forming area. In addition, the multiple rosette shape of the wire linkage area $4a$ causes a more cross-linked design of the formed wire basket unit $5a$ in its distal area, as illustrated in FIG. 7. This contributes to a further increased flexibility with respect to the bending-open of the wire linkage area $4a$ to form the wire basket unit $5a$ in its distal end area, so that a particularly blunt tipless end section can be achieved without facilitating a breaking of the material.

Figure 8:
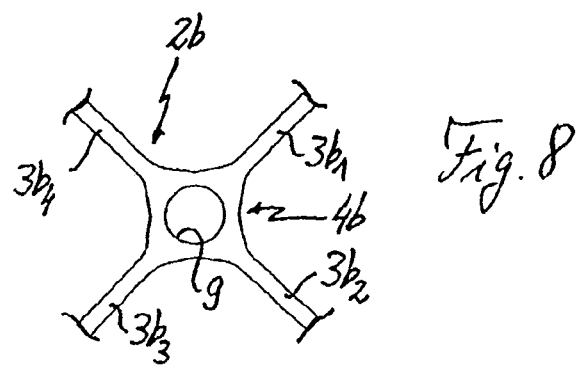
FIGS. 8 to 10 are cutout-type top views respectively of a sheet material with a cut-out wire complex with different designs of a radially interior wire linkage area in accordance with alternative embodiments of the present invention.

Depending on the demand, further variants of wire complexes cut from a sheet material can be implemented, which wire complexes have wire sections extending essentially radially from a wire linkage area. Thus, FIG. 8 shows a wire complex $2b$ which is cut out of sheet material and has four radial wire sections $3b_1$ to $3b_4$ which cohere at their radially interior end by way of a rosette-shaped wire linkage area $4b$ designed as an essentially square surface section with a circular opening 9 provided therein. With respect to the wire basket unit formed therefrom, this embodiment corresponds to the described embodiment with respect to FIGS. 13 and 14 in the older application, to which reference can be made.

Figure 9:
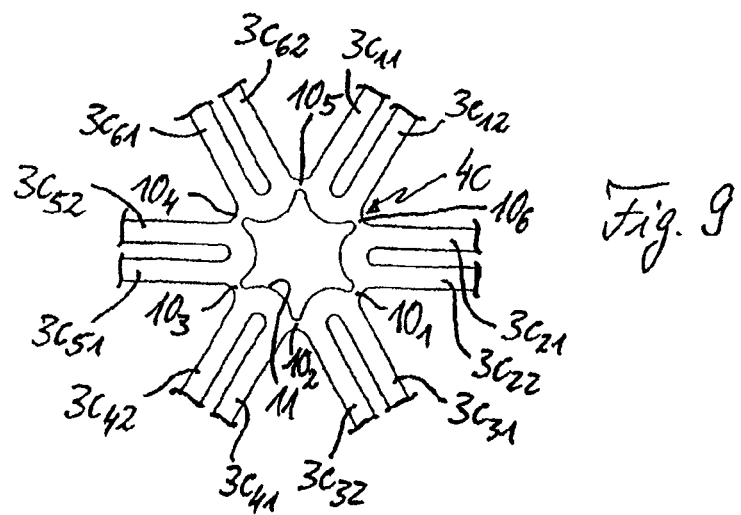

In the embodiment of FIG. 9, the wire complex contains six pairs of respectively parallel radial wire sections $3c_{11}$, $3c_{12}$, $3c_{21}$, $3c_{22}$, . . . , extending at a narrow distance from one another which have free ends on the radial exterior and cohere in the radial interior by way of a rosette-shaped wire linkage area $4c$, which consists of webs $10_1$ to $10_6$ connecting in each case two adjoining wire sections of two adjacent wire section pairs, and contains a rounded centric hexagon-shaped cutout 11.

Figure 10:
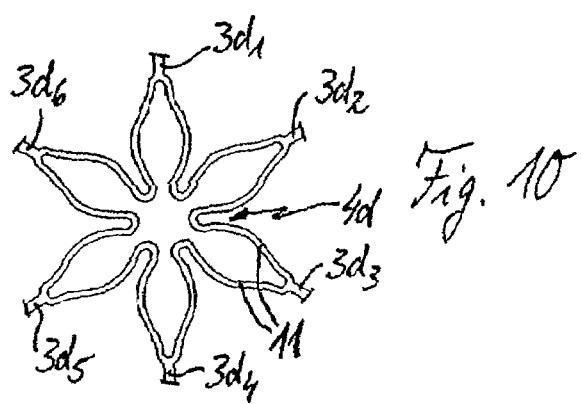

A particularly advantageous embodiment illustrated in FIG. 10 contains six wire sections $3d_1$ to $3d_6$ extending radially from an interior wire linkage area $4d$, which in this embodiment has a rosette shape illustrated in FIG. 10, where each wire section $3d_1$ to $3d_6$ is divided into two connection sections 11, in each case, two mutually facing connection sections of two adjacent wire sections change into one another in one piece in a U shape. This design of the wire linkage area $4d$ has a comparatively high flexibility because the wire linkage area $4d$ itself consists only of wire section segments. Concerning its further characteristics and advantages, this embodiment corresponds to the embodiment described in the older application with respect to FIG. 22, to which reference can be made here.

Figure 11:
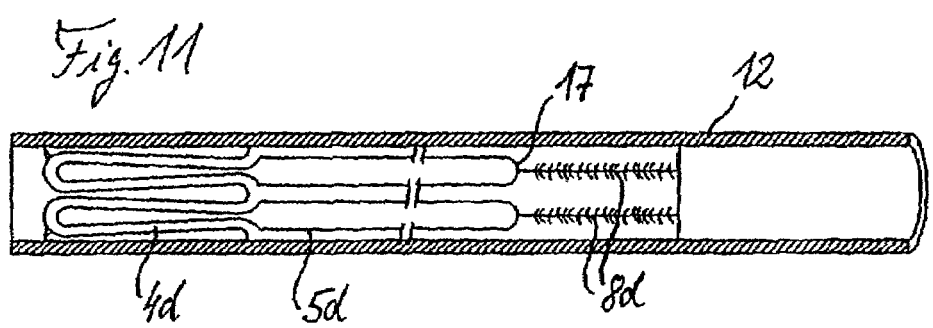
FIG. 11 is a longitudinal sectional view of a receiving sleeve with a wire basket unit of the type of FIGS. 3 and 7 accommodated therein, for the shaping of the wire basket linkage area in the manner of FIG. 10.

FIG. 11 shows a particularly advantageous application of a wire complex of the type of FIG. 10 as a wire basket unit for a medical stone catching instrument. For this purpose, the wire complex is cut out of a plane material, as explained above, for example, with respect to FIGS. 1 and 6, and, by means of a rosette-shape wire linkage area according to FIG. 10, is bent to form a corresponding wire basket unit in that the radially exterior wire section ends are bent by approximately 90° and are guided together in the proximity of a longitudinal wire basket axis and are fixed to one another, for example, as explained above concerning the embodiments of FIGS. 1 to 5 or FIGS. 6 and 7. As illustrated in FIG. 11, the wire basket unit is then pulled or pushed into a receiving sleeve 12, in which case the wire-basket-forming elastic or superelastic wire sections $3d_1$ to $3d_6$ fold together, so that the wire basket unit takes up a folded-up condition $5d$. The wire linkage area $4d$ forms a forward distal end while the guided-together wire section ends which are fixed to one another by welded connection $8d$ form a proximal rearward end area of the wire basket unit $5d$.

As further illustrated in FIG. 11, in this embodiment, the radially exterior free wire ends are modified with respect to the embodiments of FIGS. 1 to 7 in such a manner that they have a widening 17 which facilitates the mutual contact of these bent-over wire ends and the providing of the pertaining welded connections. In a conventional manner, which is not shown, an operating unit can be coupled to the proximal end area, which operating unit is axially movably arranged in the receiving sleeve 12. By advancing this operating unit, the wire basket unit can then pushed out of the receiving sleeve 12 toward the front, so that it unfolds from its folded-together condition $5d$ into a folded-open functional condition. Subsequently, if required, it can be moved back into the receiving sleeve 12, that is, can be folded together.

It is understood that a plurality of additional, not shown designs of wire complexes cut out of an essentially plane material and consisting of cohesive wire sections can be implemented according to the invention, which can then be bent to form a wire basket unit. In particular, also all embodiments illustrated and described in the above-mentioned older application can be implemented in the manner according to the invention. With respect to the characteristics and advantages of stone catching basket instruments having such multiwire basket units, reference can be made to the corresponding statements in the older application. It is an additional advantage that the cutting of the wire complex out of an essentially plane sheet material is frequently easier with respect to manufacturing and the corresponding sheet material can frequently be provided more cost-effectively than a tubular material, and that, as a result of the rosette shape of the wire linkage area, a particularly tipless basket end area can be achieved that has a high flexibility and breaking strength.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A medical stone catching basket instrument, comprising:
a multiwire basket unit with a plurality of wire sections which are connected with one another as a cohesive wire complex,
wherein
the cohesive wire complex is formed in one piece out of an essentially planar raw material,
the plurality of wire sections
extend essentially radially,
are connected at respective radially interior ends at a wire linkage area, and
are bent to form the multiwire basket unit such that the wire linkage area forms a distal end section of the medical stone catching basket instrument,
the multiwire basket unit is arranged to move between a widened condition permitting passage of particles and a drawn together condition permitting retention of particles,
the wire linkage area is rosette-shaped and is configured such that when the plurality of wire sections are bent to form the multiwire basket unit, the respective radially interior ends of the plurality of wire sections at the wire linkage area approach the wire linkage area essentially tangential to a plane perpendicular to a longitudinal axis of the multiwire basket unit to form a balloon-shaped, virtually tipless multiwire basket unit having no wires across a central region of the rosette-shaped wire linkage area, and respective radially outer ends of the plurality of wire sections opposite the respective radially interior ends are brought adjacent to one another to define adjacent pairs of wire sections,
the adjacent pairs of wire sections are connected to one another at their respective radially outer ends, and
a first wire section of each pair of the plurality of wire sections is not connected to a second wire section of the same pair at the rosette-shaped wire linkage area.

2. The medical stone catching basket instrument of claim 1, wherein
the multiwire basket unit is formed of a superelastic material.

3. The medical stone catching basket instrument of claim 2, wherein
the multiwire basket unit is arranged to fold together radially to be received in a receiving sleeve.

4. The medical stone catching basket instrument of claim 1, wherein
the wire linkage area has a multiple rosette shape.

5. The medical stone catching basket instrument of claim 4, wherein
the multiwire basket unit is arranged to fold together radially to be received in a receiving sleeve.

6. The medical stone catching basket instrument of claim 1, wherein
respective radially exterior ends of the plurality of wire, sections are bent over in a basket shape and are fixed to one another.

7. The medical stone catching basket instrument of claim 6, wherein
the multiwire basket unit is arranged to fold together radially to be received in a receiving sleeve.

8. The medical stone catching basket instrument of claim 1, wherein
the multiwire basket unit is arranged to fold together radially to be received in a receiving sleeve.

* * * * *